United States Patent [19]

Lang

[11] 4,153,065

[45] May 8, 1979

[54] AZO DERIVATIVES OF PYRIDINE N-OXIDE FOR USE IN HAIR DYE COMPOSITIONS

[75] Inventor: Gérard Lang, Epinay-Sur-Seine, France

[73] Assignee: L'Oreal, Paris, France

[21] Appl. No.: 806,817

[22] Filed: Jun. 15, 1977

Related U.S. Application Data

[60] Continuation-in-part of Ser. No. 659,145, Feb. 18, 1976, abandoned, which is a division of Ser. No. 370,651, Jun. 18, 1973, Pat. No. 3,955,918.

[30] Foreign Application Priority Data

Jun. 19, 1972 [LU] Luxembourg .................... 65539

[51] Int. Cl.$^2$ .................... D06P 3/00; A45D 7/00
[52] U.S. Cl. .................... 132/7; 8/10; 8/10.1; 8/17; 8/41 R
[58] Field of Search .................... 8/10.1, 10, 41 R, 17; 132/7

[56] References Cited

U.S. PATENT DOCUMENTS

| 3,100,766 | 8/1963 | Lewis | 260/146 |
|---|---|---|---|
| 3,118,871 | 1/1964 | Brody et al. | 260/156 |
| 3,249,597 | 5/1966 | Dehn et al. | 260/156 |
| 3,368,941 | 2/1968 | Boosen | 8/10.1 |
| 3,386,991 | 6/1968 | Gerber | 260/156 |
| 3,393,190 | 7/1968 | Stright | 260/155 |
| 3,617,179 | 11/1971 | Lewis | 8/42 D |
| 3,955,918 | 5/1976 | Lang | 8/10 |

FOREIGN PATENT DOCUMENTS

1473787 3/1967 France.

*Primary Examiner*—A. Lionel Clingman
*Attorney, Agent, or Firm*—Cushman, Darby & Cushman

[57] ABSTRACT

Compositions for dyeing human hair contain in an aqueous or hydroalcoholic solution an azo derivative of pyridine N-oxide as a hair dye present in amounts of 0.001–1 weight percent of said composition which has a pH ranging from 3–9.5. Certain of said azo derivatives of pyridine N-oxide are new compounds.

16 Claims, No Drawings

AZO DERIVATIVES OF PYRIDINE N-OXIDE FOR USE IN HAIR DYE COMPOSITIONS

CROSS REFERENCE TO RELATED APPLICATIONS

This is a continuation-in-part of U.S. Pat. application Ser. No. 659,145, filed Feb. 18, 1976, abandoned which is relied upon and incorporated by reference herein; said Ser. No. 659,145 is in turn a divisional application of Ser. No. 370,651, filed June 18, 1973 now U.S. Pat. No. 3,955,918.

The present invention relates to dye compositions for human hair, characterized by the fact that they include in solution one or more compounds of the formula:

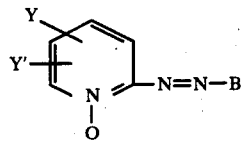

(I)

wherein Y and Y' each represent hydrogen, halogen, lower alkyl having 1-4 carbon atoms, lower alkoxy having 1-4 carbon atoms, nitro or carboxyl;

B represents a member selected from the group consisting of

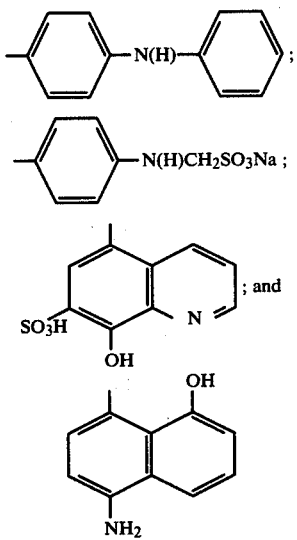

Preferably, Y and Y' of formula I each represent hydrogen or lower alkyl of 1 to 4 carbon atoms. Compounds of formula I may be used in the salt form and may be used as the methylsulfate, iodide or perchlorate salt of a compound of formula I.

It has now been discovered that these dyes exhibit an excellent affinity for human hair and provide luminous and stable colorations ranging from yellow to blue.

The dyes of formula I exhibit, relative to known disazo dyes for coloring hair, the advantage of being more soluble in water and of providing a significantly wider range of colors, especially since the colorations attainable range from yellow to blue.

The compositions of the present invention are aqueous or hydroalcoholic solutions that can easily be prepared by dissolving in water or in a mixture of water and alcohol, one or more compounds of formula I. The alcohol employed in said compositions is generally present in amounts of about 5-70 percent by weight thereof and is generally ethanol or isopropanol.

The concentration of the compounds of formula I in the dye composition of the present invention can vary widely because of their good affinity for hair. This concentration is generally between about 0.001-1 percent by weight of said composition.

The pH of the composition according to the present invention is generally between about 3-9.5; and the pH can be adjusted to the desired value by the addition to said composition of an acid such as orthophosphoric or acetic acid, or of a base such as triethanolamine or ammonia. Obviously, other pH adjusting agents conventionally employed in cosmetic compositions can also be utilized.

The composition of the present invention can also include various conventionally employed cosmetic adjuvants such as wetting agents, dispersing agents, swelling agents, penetrating agents, emolients and perfumes. Further, the composition of the present invention can be packaged under pressure in an aerosol bomb or container with a conventional liquefied aerosol propellant, such as fluoronated hydrocarbon including dichlorodifluoromethane, trichloromonofluoromethane and mixtures thereof.

The compositions of the present invention can also include other direct dyes such as azo dyes anthraquinone dyes, nitro dyes of the benzene series, indoanilines, indophenols, indamines, or mixtures of dyes of formula I.

The composition of the present invention can be utilized to provide a durable dyeing of the hair, in which case it is applied to the hair and left in contact therewith for a period of about 3-30 minutes. This application is followed by rinsing, washing and drying the thus dyed hair.

The compositions of the present invention can also be employed as a rinse lotion which imparts to the hair a light coloration, in which case they are applied to previously washed hair and the application of the same is not followed by a rinsing of the hair.

The compositions of the present invention can also be employed as hair setting lotions which both impart to the hair a light coloration and improve the holding power of the hair set. In this case, the compositions are present in the form of a hydroalcoholic solution containing at least one cosmetic film-forming resin having a molecular weight ranging from about 10,000 to 3,000,000. These compositions are generally applied to previously washed and rinsed wet hair which is then rolled up on curlers and dried.

The cosmetic film-forming resins usefully employed in said hair setting lotions are present therein in amounts of about 1-3 percent by weight of said composition and include for instance, polyvinylpyrrolidone having a molecular weight between 40,000 and 400,000; 70-30%/30-70% vinylpyrrolidone/vinyl acetate copolymers; copolymers of vinyl acetate and an unsaturated carboxylic acid such as crotonic acid (90:10) having a molecular weight ranging from about 20,000-50,000, preferably about 45,000-50,000; copolymers of maleic anhydride and butyl vinyl ether copolymers resulting from the polymerization of vinyl acetate (75-85%), crotonic acid (5-15%) and an acrylic or methacrylic ester (5-15%) or an alkyl vinyl ether (5-15%); copolymers resulting from the copolymerization of vinyl acetate (63-88%), crotonic acid (5-15%) and (a) (5-25%) of a vinyl ester of an acid with a long carbon chain having 10-22 carbon atoms or (b) (5-25%) of an allyl or methallyl ester of an acid with a long carbon chain having 10-22 carbon atoms; copolymers resulting from the copolymerization of 65-80% of an ester of an unsaturated alcohol having from 2 to 12 carbon atoms and a carboxylic acid having from 2 to 5 carbon atoms, 7-12% of an unsaturated acid having from 4 to 20 carbon atoms and 10-20% of at least an ester of a saturated alcohol having from 8 to 18 carbon atoms and an unsaturated acid having from 4 to 20 carbon atoms.

The hair setting lotions of the present invention generally contain about 20-70 weight percent low molecular weight alcohol such as ethanol or isopropanol.

Consequently the present invention also has for an object a new industrial product which is a compound of the formula I (above), the salts of said compound and the O-alkyl derivatives thereof.

The componds of the present invention can be obtained in accordance with the conventional procedures by condensing a diazonium salt of the formula

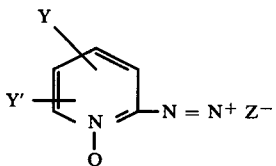

wherein Y and Y' have the meanings given above and Z⁻ is an anion selected from the group consisting of chloride, orthophosphate and sulfate with a coupler selected from the group consisting of

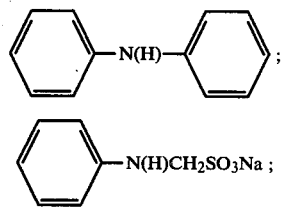 (a)

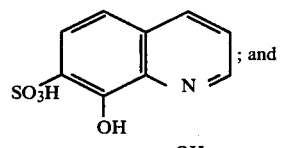 (b)

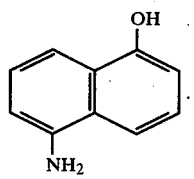 (c)
; and (d)

The following examples are given to illustrate the different aspects of the present invention. All parts and percentages are by weight unless otherwise specified.

EXAMPLE 1

Preparation of (4'-phenylaminobenzene)-2-azo(3-methyl pyridine N-oxide of the formula

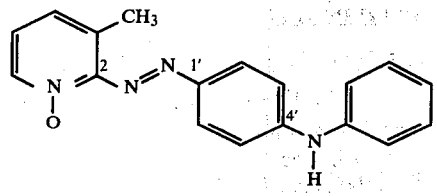

2-amino-3-methyl-pyridine-N-oxide is prepared according to Adams' procedure in *J. Am. Chem. Soc.*, 76, p. 2785 (1954). 15 cm³ of a 7.5 N sodium nitrite solution, cooled to a temperature of between 0° and 5° C. was added to a solution of 0.1 mole of said pyridine-N-oxide dissolved in 90 cm³ of 5 N HCl. The reaction was allowed to proceed for 30 minutes, and then excess nitrous acid was destroyed by adding sulfamic acid to the composition.

0.1 mole of diphenylamine in 10 cm³ acetic acid was added slowly to the solution of the diazonium salt which was maintained at a temperature of 5° C. during the addition. The reaction mixture was then stirred for 30 minutes, and subsequently this reaction mixture was neutralized by the addition of dilute base. The dye is filtered, washed with water and then dried. After recrystallization from ethyl acetate, the compound has a melting point of 182° C.

|                | C     | H    | N     |
|----------------|-------|------|-------|
| Theoretical %  | 71.05 | 5.27 | 18.42 |
| Experimental % | 70.03 | 5.37 | 18.44 |

EXAMPLE 2

Preparation of the compound of the formula

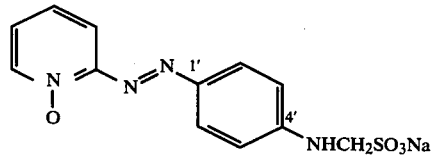

0.11 mole of

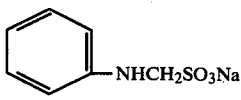

was dissolved in 17 cm³ water 53 g of sodium acetate was added to the solution which was thereafter cooled to 5° C. To said cooled solution, a cooled solution of the chloride of 2-diazonium N-pyridine oxide was added slowly; said diazonium salt had been prepared according to the following procedure:

0.1 mole of 2-amino-pyridine-N-oxide, prepared by the method described by Adams in *J. Am. Chem. Soc.*, 76 p 2785 (1954), which is hereby incorporated by reference herein, was dissolved in 90 cm³ of 5 N HCl. While maintaining the resulting solution at 0°-5° C., 15 cm³ of 7.5 N sodium nitrite was added. The mixture was allowed to react for 30 minutes, after addition, and excess nitrous acid was destroyed by the addition of sulfamic acid.

Then 130 g of crystalline sodium acetate was added and left to react for about one hour. The resulting dye was filtered and dried and when, subsequently crystallyzed, was characterized by a melting point of 160° (with decomposition).

Analysis $C_{12}H_{11}N_4O_4SNa, 3H_2O$

|  | C | H | N |
|---|---|---|---|
| Theoretical % | 37.50 | 4.32 | 14.55 |
| Experimental % | 37.99 | 3.46 | 14.26 |

EXAMPLE 3

Preparation of the compound of the formula

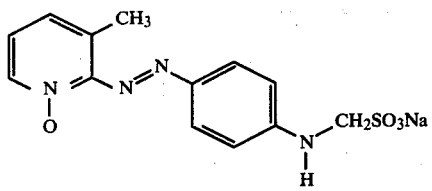

This compound was prepared in a manner similar to that described in Example 2, except that the diazotized amine was 2-amino 3-methyl pyridine N-oxide. The resulting compound melted at 140° C. after recrystallization from water.

Analysis $C_{13}H_{13}N_4O_4SNa$

|  | C | H | N |
|---|---|---|---|
| Theoretical % | 39.20 | 4.77 | 14.05 |
| Experimental % | 39.63 | 4.66 | 13.92 |

EXAMPLE 4

Preparation of (8'-hydroxy 7'-sulfonate-quinoline)-5':2-azo(pyridine-N-oxide) of the formula

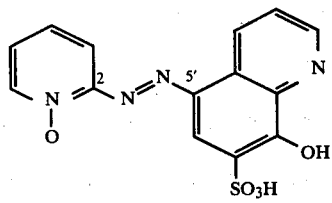

0.1 mole of 2-amino-pyridine-N-oxide was diazotized according to the method described in Example 2.

Then 0.1 mole of the acid of 7-sulfonate-8-hydroxyl-quinoline is dissolved in 150 cm³ of water containing 0.2 mole of base. Then the solution is cooled to 5° C., and the, dropwise, at said low temperature, the cooled solution of the chloride of 2-diazonium-pyridine-N-oxide was added thereto. The mixture was allowed to reach ambient temperatures, then filtered, washed with water and dried. The dye, recrystallized from water had a melting point of 245° C.

Analysis $C_{14}H_{10}N_4O_5S$

|  | C | H | N |
|---|---|---|---|
| Theoretical % | 48.55 | 2.89 | 16.18 |
| Experimental % | 48.71 | 3.63 | 16.07 |

EXAMPLE 5

Preparation of (4'-amino-8'-hydroxy naphthyl) 1':2 azopyridine-N-oxide of the formula

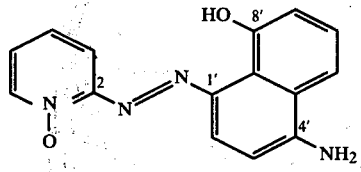

0.1 mole of 2-amino pyridine N-oxide was diazotized in a manner identical to that described in Example 2.

1-amino, 5-hydroxy-naphthalene (0.1 mole) was dissolved in 500 cm³ of 50% alcohol admixed with 100 cm³ of acetic acid. The solution was cooled to 5° C., and then at said reduced temperature a cooled solution of the chloride of 2-diazonium pyridine-N-oxide was added dropwise thereto. The mixture was subsequently stirred for 30 minutes, and then 50 g of sodium acetate was added thereto. The reaction mixture was filtered; the precipitate was washed with water and dried. The dye, purified by dissolution in acetic acid with subsequent precipitation by the addition of ether, melted at 260° C. (with decomposition).

EXAMPLE 6

Preparation of (4'-aminobenzene) 1':2 azo pyridine-N-oxide of the formula

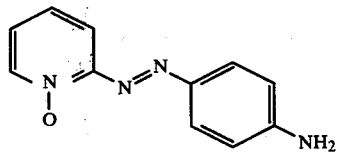

0.1 mole of the compound obtained in Example 2 was dissolved in 200 cm³ of 10% ammonia solution and warmed for 5 hours at 60° C. Then the mixture was cooled and filtered; the precipitate was washed with water and dried. The dye, recrystallized from methanol melted at 300° C. with decomposition.

Analysis $C_{11}H_{10}N_4O$

|  | C | H | N |
|---|---|---|---|
| Theoretical % | 61.70 | 4.67 | 26.17 |
| Experimental % | 61.79 | 4.93 | 25.99 |

EXAMPLE 7

Preparation of (4'-dimethylamino 2'-methyl benzene) 1':2 azopyridine-N-oxide of the formula

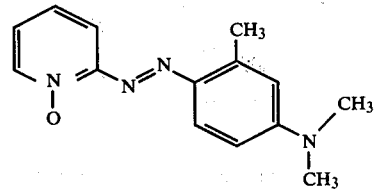

This compound was obtained according to a method similar to that of Example 1. In this case, the diazotized amine was 2-amino pyridine-N-oxide and the coupler was N,N-dimethyl meta-toluidine. The dye melted at 165° C. after recrystallization from methanol.

Analysis $C_{14}H_{16}N_4O$

|  | C | H | N |
|---|---|---|---|
| Theoretical % | 65.65 | 6.25 | 21.85 |
| Experimental % | 65.37 | 6.20 | 21.51 |

EXAMPLES OF FORMULATIONS OF THE FOREGOING DYESTUFFS

| Dye of Example 2 | 1 g |
|---|---|
| Polyvinylpyrrolidone/vinyl acetate copolymer (60/40) | 2.5 g |
| Ethanol | 70 g |
| Citric acid, q.s. pH = 3 | |
| WAter q.s.p. | 100 cm³ |

This solution was applied as a hair setting lotion to stripped hair and imparted to the hair a rust color.

| Dye of Example 3 | 0.1 g |
|---|---|
| Polyvinylpyrrolidone/vinyl acetate copolymer (30/70) | 1 g |
| Ethanol | 20 g |
| Citric acid, q.s. pH = 6 | |
| Water q.s.p. | 100 cm³ |

This solution, applied as a hair setting lotion to stripped hair imparted to the hair a yellow gold color.

| Dye of Example 7 | 0.002 g |
|---|---|
| Dye of Example 5 | 0.001 g |
| Butyl monoester of maleic anhydride/methyl vinyl copolymer | 1 g |
| Ethanol | 50 g |
| Triethyanolamine q.s. pH = 8 | |
| Water q.s. | 100 cm³ |

This solution, applied to stripped hair, as a hair setting lotion, imparted to the hair a platinum tone.

| Composition of Example 6 | 0.2 g |
|---|---|
| Dyestuff of Example 1 | 0.2 g |
| Polyvinylpyrrolidone PM = 40.000 | 1 g |
| Isopropanol | 20 g |
| Citric acid, q.s. pH = 4 | |
| Water, q.s. | 100 cm³ |

This solution, applied as a hair setting lotion, to stripped hair, imparted to the hair a red coloration.

| Dye of Example 5 | 0.3 g |
|---|---|
| Dyestuff of Example 2 | 0.1 g |
| N-(2'-chloro 4'-hydroxy phenyl) 2-methyl 5-ureido benzoquinone imine | 0.05 g |
| Polyvinylpyrrolidione PM = 40.000 | 1 g |
| Citric acid, g.s. pH = 3 | |
| Water,g.s. | 100 cm³ |

The hair was then rinsed, shampooed, rinsed again and dried.

The hair, dyed in this manner, was characterized by a auburn color.

| Dye of Example 1 | 0.5 g |
|---|---|
| Butylcellusolve | 8 g |
| Propylene glycol | 8 g |
| Remcopal 334 | 22 g |
| Remcopal 349 | 22 g |
| Ammonia at 22° Be. | 10 g |
| Water, q.s. | 100 cm³ |

The aforementioned composition was admixed, just prior to use, with an equal amount of hydrogen peroxide (20 volumes). After 30 minutes, the solution having been applied to stripped hair, imparted to the hair a blond gold coloration.

| Dyestuff of Example 3 | 0.05 g |
|---|---|
| Dyestuff of Example 4 | 0.15 g |
| Ethylcellusolve | 10 cm³ |
| Triethanolamine, q.s. pH = 9 | |
| Water, q.s. | 100 cm³ |

This composition, applied to stripped hair and left thereon for 15 minutes, imparted to the hair a pale rose coloration.

| Dye of Example 3 | 0.8 g |
|---|---|
| 2-amino 4,4'-dihydroxy azobenzene | 0.05 g |
| di[β-morpholino ethyl amino]-1,4 anthraquinone | 0.02 g |
| Ethanol | 10 g |
| Water, q.s. | 100 cm³ |

This solution, applied to stripped hair for 5 minutes, imparted to the hair, after rinsing and washing, a yellow light ocre color.

Thus, it is apparent that there has been provided, in accordance with the invention, a series of dyestuffs that fully satisfies the objects, aims and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications and variations as fall within the spirit and broad scope of the appended claims.

What is claimed is:

1. A dye composition for human hair comprising a solution in a solvent selected from the group consisting of water and aqueous alcohol solution of about 0.001–1 percent by weight of at least one dye selected from the group consisting of

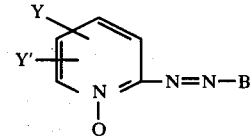

(I)

wherein Y and Y' each represent hydrogen, halogen, lower alkyl having 1–4 carbon atoms, lower alkoxy having 1–4 carbon atoms, nitro or carboxyl;

B represents a member selected from the group consisting of

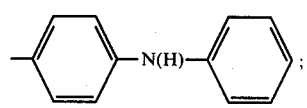

(a)

-continued

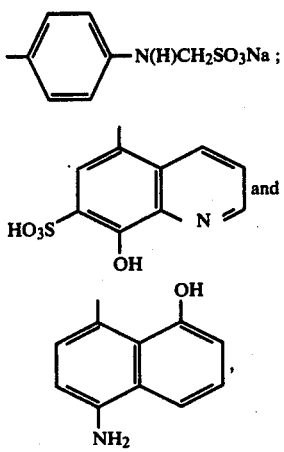

said composition having a pH ranging from 3-9.5.

2. The composition of claim 1, wherein B is (a) or (b).

3. The composition of claim 1, wherein B is (c) or (d).

4. The composition of claim 1, wherein Y and Y' each represent hydrogen or alkyl of 1 to 4 carbon atoms.

5. The composition of claim 4, wherein said dye has the formula

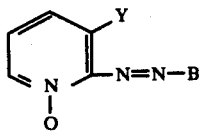

6. The composition of claim 5, wherein Y is said alkyl.

7. The composition of claim 4, wherein at least one of Y or Y' is methyl.

8. The composition of claim 1, which also includes at least one other direct hair dye.

9. The composition of claim 8, wherein said other direct hair dye is selected from the group consisting of azo dyes, anthraquinone dyes, nitro dyes of the benzene series, indoanilines, indophenols indamines.

10. The composition of claim 1 which includes a lower aliphatic alcohol containing 1 to 4 carbon atoms in amounts of about 5 to 70% by weight of said composition.

11. The composition of claim 10, wherein said alcohol is selected from the group consisting of ethanol and isopropanol.

12. The composition of claim 10 which also includes a cosmetic film-forming resin in amounts of about 1 to 3% by weight of said composition and wherein said alcohol is present in amounts of about 20 to 70% by weight of said composition.

13. The composition of claim 12, wherein said cosmetic film-forming resin is selected from the group consisting of polyvinylpyrrolidone, a copolymer of vinyl acetate and crotonic acid, a copolymer of vinylpyrrolidone and vinyl acetate and a copolymer of maleic anhydride and butyl vinyl ether.

14. The composition of claim 13, wherein said resin is selected from the group consisting of polyvinylpyrrolidone, a copolymer of vinyl acetate and vinylpyrrolidone and a copolymer of maleic anhydride and butyl vinyl ether.

15. A process for dyeing human hair comprising applying to said hair in amounts effective to dye said hair the composition of claim 1, permitting said composition to remain in contact with said hair for a period ranging between about 3 to 40 minutes, rinsing, washing and drying said hair.

16. A process of dyeing human hair comprising applying to previously washed and rinsed hair in amounts effective to dye said hair the composition of claim 12, rolling said hair up on curlers and drying said hair.

* * * * *